(12) United States Patent
Dennis, Jr. et al.

(10) Patent No.: US 10,350,362 B2
(45) Date of Patent: Jul. 16, 2019

(54) AUTOMATIC MEDICATION INJECTION DEVICE WITH VISIBLE INDICATION OF INJECTING PROGRESS

(71) Applicant: Eli Lilly and Company, Indianapolis, IN (US)

(72) Inventors: Joseph Daniel Dennis, Jr., Wyoming, OH (US); Jessica Diane Modlich, Columbus, OH (US)

(73) Assignee: Eli Lilly and Company, Indianapolis, IN (US)

( * ) Notice: Subject to any disclaimer, the term of this patent is extended or adjusted under 35 U.S.C. 154(b) by 103 days.

(21) Appl. No.: 15/502,350

(22) PCT Filed: Aug. 7, 2015

(86) PCT No.: PCT/US2015/044219
§ 371 (c)(1),
(2) Date: Feb. 7, 2017

(87) PCT Pub. No.: WO2016/025316
PCT Pub. Date: Feb. 18, 2016

(65) Prior Publication Data
US 2017/0224926 A1 Aug. 10, 2017

Related U.S. Application Data

(60) Provisional application No. 62/037,826, filed on Aug. 15, 2014.

(51) Int. Cl.
*A61M 5/315* (2006.01)
*A61M 5/20* (2006.01)
*A61M 5/32* (2006.01)

(52) U.S. Cl.
CPC ...... *A61M 5/31568* (2013.01); *A61M 5/2033* (2013.01); *A61M 5/31526* (2013.01);
(Continued)

(58) Field of Classification Search
CPC ............ A61M 5/31568; A61M 5/2033; A61M 5/31526; A61M 5/31561
See application file for complete search history.

(56) References Cited

U.S. PATENT DOCUMENTS 6,290,678 B1 * 9/2001 Aydelotte ............ A61M 5/3129
604/187
6,692,469 B1 2/2004 Weekes et al.
(Continued)

FOREIGN PATENT DOCUMENTS

FR        2990867       11/2013
WO     2006079918        8/2006
(Continued)

OTHER PUBLICATIONS

Patent Cooperation Treaty International Search Report and Written Opinion of the International Searching Authority pertaining to International Application No. PCT/US2015/044219, dated Oct. 20, 2015.

*Primary Examiner* — Nathan R Price
*Assistant Examiner* — Melissa A Snyder
(74) *Attorney, Agent, or Firm* — M Daniel Spillman

(57) ABSTRACT

An automatic medication injection device (20) including injecting progress indicators (82-85) visible along a periphery of the device housing (23). The injecting progress indicators include a flag element (100) which is movable as a drive mechanism (60) of the device advances a sealing plunger (58) within a container of medication (50). The injecting progress indicators are configured to indicate sequentially during a single injection as the flag element moves to cooperatively complete different injecting progress indicators at different times during the single injection, whereby injecting progress of the injection may be monitored by a user.

14 Claims, 5 Drawing Sheets

(52) U.S. Cl.
CPC .... *A61M 5/31561* (2013.01); *A61M 5/31593* (2013.01); *A61M 5/3202* (2013.01); *A61M 2205/0216* (2013.01); *A61M 2205/6081* (2013.01)

(56) References Cited

U.S. PATENT DOCUMENTS

| | | | |
|---|---|---|---|
| 6,929,619 | B2 | 8/2005 | Fago et al. |
| 7,252,651 | B2 | 8/2007 | Haider et al. |
| 2009/0299278 | A1* | 12/2009 | Lesch, Jr. ........... A61M 5/2033 604/68 |
| 2012/0037530 | A1* | 2/2012 | Boyd ................... A61M 5/24 206/459.5 |
| 2012/0089098 | A1 | 4/2012 | Boyd et al. |
| 2013/0317434 | A1 | 11/2013 | Fabien et al. |
| 2014/0323980 | A1 | 10/2014 | Cronenberg et al. |
| 2016/0022908 | A1 | 1/2016 | Giambattista et al. |

FOREIGN PATENT DOCUMENTS

| | | |
|---|---|---|
| WO | 2008145171 | 12/2008 |
| WO | 2011047298 | 4/2011 |
| WO | 2012085031 | 6/2012 |
| WO | 2013077800 | 5/2013 |
| WO | 2013153011 | 10/2013 |
| WO | 2014053496 | 4/2014 |

\* cited by examiner

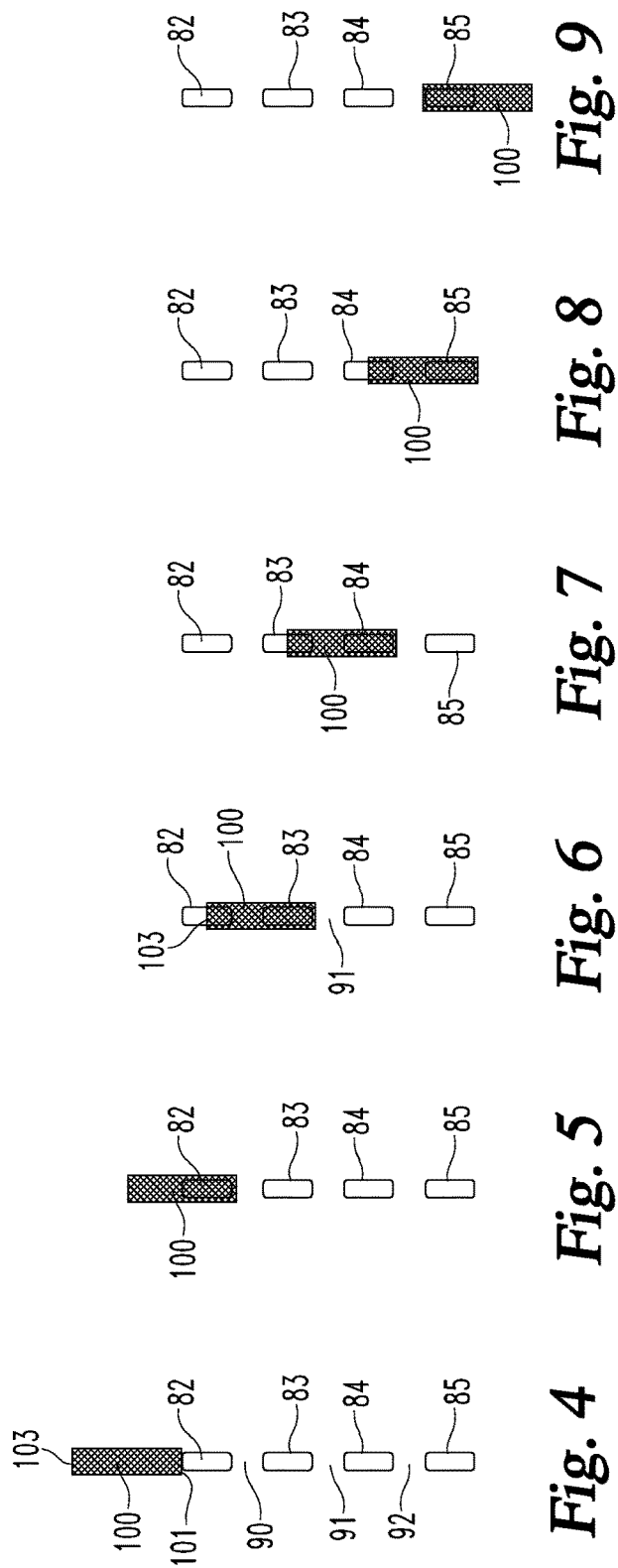

AUTOMATIC MEDICATION INJECTION DEVICE WITH VISIBLE INDICATION OF INJECTING PROGRESS

BACKGROUND OF THE INVENTION

The present invention pertains to medication injection devices, and, in particular, to medication injection devices having features that provide to the users of such devices visible information as to use.

Patients suffering from a number of different diseases frequently must inject themselves with medications. A variety of devices have been proposed to facilitate these injections. One type of device is an automatic medication injection device. This type of device typically includes a trigger that when operated by a user causes the device to automatically insert into the user a needle of a syringe that prior to triggering was disposed within the device housing, and then the device automatically injects a dose of medication through that inserted needle. In some cases, an automatic injection device does not so insert the needle into the user, but does, when triggered, automatically inject a dose of medication through the needle that has been manually inserted by the user.

One potential shortcoming with using automatic injection devices relates to the fact that some users may be unsure they are using the devices correctly. Without some sort of feedback from the device when it is being used, a user may question whether an injection has commenced or whether it is finished. Uncertainty in the user about an injection being completed is particularly likely in cases where the injection takes a relatively long time to complete, possibly such as due to a large volume dose or a high viscosity dose of medication being delivered.

Some known devices such as disclosed in WO 2014/053496 and US 2013/0317434 provide visual indicators associated with device use. However, known indicators that do not provide sufficient updates during a medication injection, or that rely on a user looking for a portion of a sealing plunger that resides within a cartridge or fluid container barrel, may not be adequate or convenient for some users.

Thus, it would be desirable to provide an automatic medication injection device with a visible indicator which can overcome one or more of these and other shortcomings of the prior art.

BRIEF SUMMARY OF THE INVENTION

In one form thereof, the present invention provides an automatic medication injection device including a user grippable housing, a container of medication, a drive mechanism and a plurality of injecting progress indicators. The user grippable housing has a length extending in an axial direction between a proximal end and a distal end. The container of medication includes an outlet that is disposed proximally of the housing proximal end at least during injection. The container includes a barrel and a sealing plunger, which sealing plunger is in sealing engagement with the barrel. The drive mechanism is within the housing and when triggered automatically advances the sealing plunger proximally within the container to force medication from the container outlet. The plurality of injecting progress indicators are visible along a periphery of the housing. At least one of the plurality of injecting progress indicators is located distally of the container during an injection. The injecting progress indicators include a flag element movable as the drive mechanism advances the sealing plunger proximally within the container. The plurality of injecting progress indicators are configured to indicate sequentially in an axial direction during a single injection as the flag element moves to cooperatively complete different injecting progress indicators at different times during the single injection, whereby injecting progress of the injection may be monitored by a user.

One advantage of the present invention is that an automatic medication injection device may be provided with a visible indicator of injecting progress.

Another advantage of the present invention is that an automatic medication injection device may be provided with a visible indicator of injecting progress that updates during the medication delivery.

Still another advantage of the present invention is that an automatic medication injection device may be provided having a visible indicator of injecting progress that is easily readable due to its form as well as its positioning within the device housing.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIG. 4 is a schematic front view of the injecting progress indicators shown separate from the remainder of the device and as configured when the device is arranged as in FIG. 3;

FIG. 5 is a schematic front view similar to the view of FIG. 4 but as configured at a later time during injection than as shown in FIG. 4;

FIG. 6 is a schematic front view similar to the view of FIG. 5 but as configured at a later time during injection than as shown in FIG. 5;

FIG. 7 is a schematic front view similar to the view of FIG. 6 but as configured at a later time during injection than as shown in FIG. 6;

FIG. 8 is a schematic front view similar to the view of FIG. 7 but as configured at a later time during injection than as shown in FIG. 7;

FIG. 9 is a schematic front view similar to the view of FIG. 8 but as configured at a later time at which the complete medication dose of the device has been injected through the needle;

Figure 1:
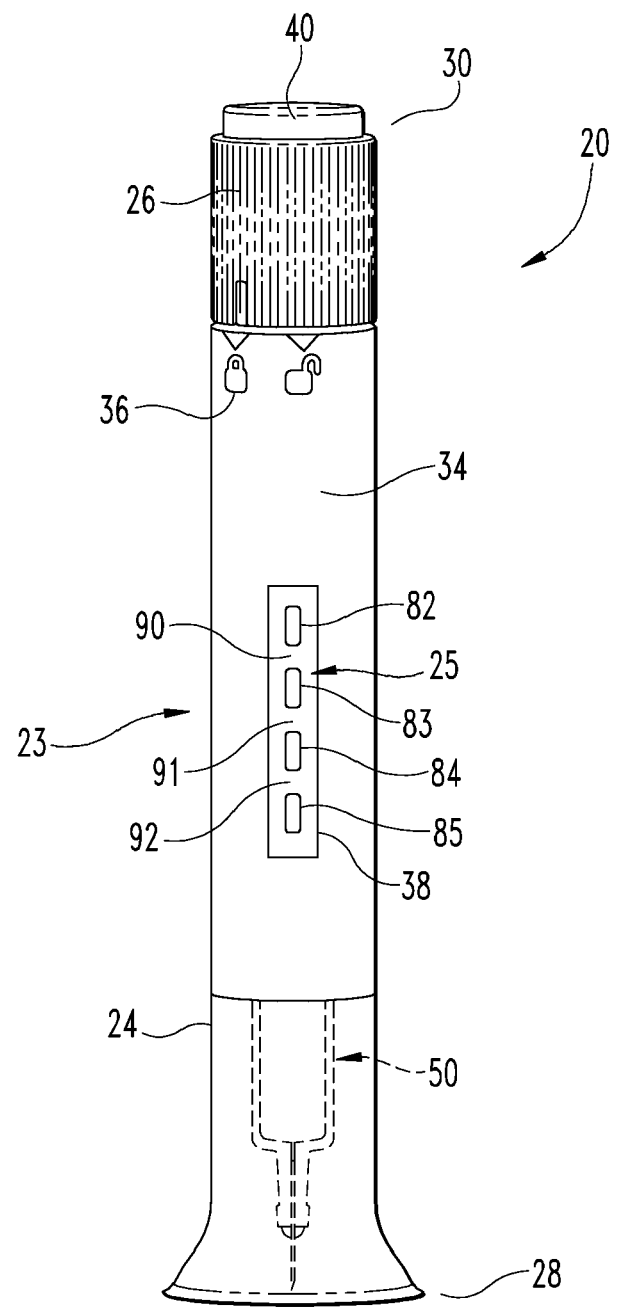
FIG. 1 is a front view of an automatic injection device with a visible injecting progress indicator of the present invention shown prior to use.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
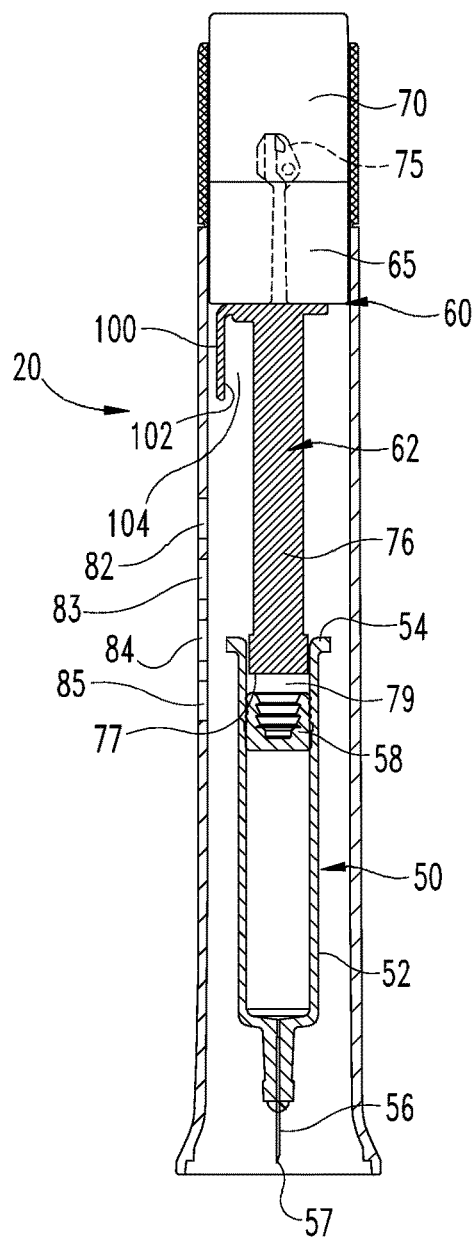
FIG. 2 is a cross-sectional side view of the device of FIG. 1 prior to use, wherein portions of the device are omitted or shown schematically.
Figure 3:
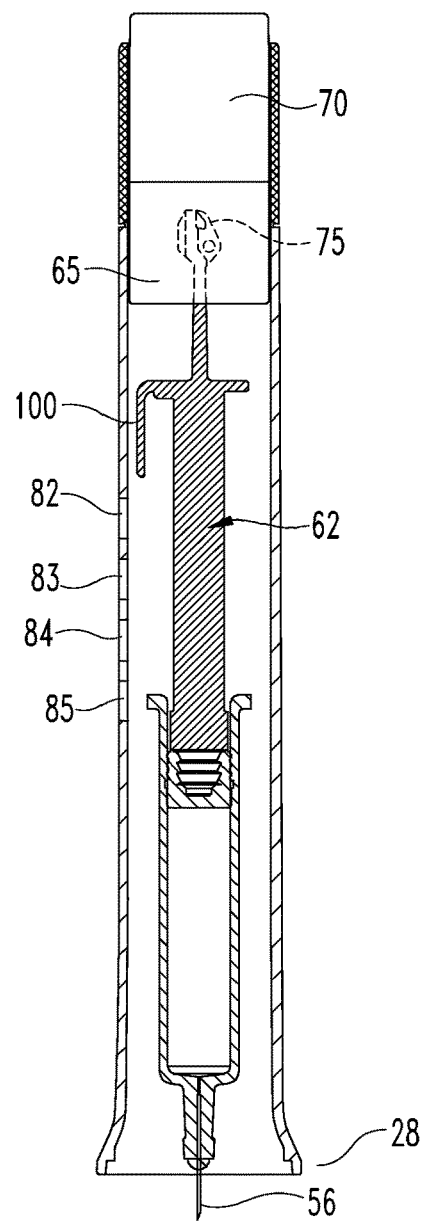
FIG. 3 is a cross-sectional side view of the device of FIG. 2 after triggering and at a point when the needle has been extended for user penetration but before the start of the medication dose actually injecting into the user through the needle.

Referring now to FIGS. 1, 2 and 3, there are shown different views of a first embodiment of an automatic medication injection device with injecting progress indicators of the present invention. The automatic medication injection device, generally designated 20, is shown and described as a device that when its trigger is manually operated, its needled syringe 50 is automatically driven downward such that its injection needle projects beyond the bottom end of the device housing to penetrate the user. The device then proceeds to inject automatically, that is without further user action, the entire medication contents of the device through the injection needle.

The injecting progress indicators, generally indicated at 25, find beneficial application in the device 20 described herein, but such application is merely illustrative and not intended to be limiting. The injecting progress indicators can be used in many different types of automatic medication injection devices where its benefits are desired, including devices in which the insertion of the needle is manually performed but the forcing of the medicine through such needle is automatic once triggered, and in devices in which more than a single dose is dispensable therefrom.

It will be appreciated from the following description that device 20 is conceptually similar in various aspects to the devices disclosed in International Publication Number WO 2014/062488, which publication is incorporated herein by reference in its entirety.

Device 20 includes an outer housing 23, which is grippable by a user and in which are operationally disposed working components of the device. The outer housing 23 includes a safety sleeve 26 and a main body 24 that together form the height of the outer housing extending in the axial direction between proximal end 28 and distal end 30. The main body 24 is shown formed of a transparent plastic, and an opaque wrap or label 34 around the upper portion of the main body 24 hides working device components protectively encased within the housing. Label 34 may include information, such as icons 36 associated with locking, or product details or instructions for use. Label 34 includes a slot or opening 38 through which injecting progress indicators 25 are visible to a user of device 20 along the exterior or periphery of the housing 23. Instead of an opening 38, the label 34 instead could be transparent at that region.

Safety sleeve 26 is rotatable by the user relative to main body 24 between locked and unlocked conditions as indicated at icons 36. A button 40 that is part of the trigger assembly protrudes in the axial direction from the top or distal end 30 of the housing. When properly rotationally oriented by rotation of sleeve 26, button 40 is unlocked such that it can be depressed in the proximal direction to start the automatic injection function of device 20. As used herein, distal and proximal refer to axial locations relative to an injection site when the device is oriented for use at such site, whereby, for example, proximal end of the housing refers to the housing end that is closest to such injection site. The shown triggering button 40 is the manner in which device 20 is triggered, but other triggering designs are known and can be used in devices with injecting progress indicators. A needle cap that is typically provided on device 20 and then removed prior to use is not shown in the Figures.

As further shown abstractly in FIG. 2, device 20 includes a medication-filled container provided in the form of a syringe, generally designated 50, that is axially movable within the housing 23. Syringe 50 is of a conventional design and includes a transparent barrel 52 with a flange 54 at its distal end, an injection needle 56 that serves as an outlet for the barrel 52, and a sealing plunger 58. Injection needle 56 is mounted at the proximal end of barrel 52 and in fluid communication with the medication contents of the barrel. Sealing plunger 58 is an elastomeric sealing member having an outer radial periphery adapted to slidably and sealingly engage the inner circumference or inner radial periphery of the barrel 52 so as to seal medication within the barrel below the proximal face of the sealing plunger 58.

Syringe 50 is disposed completely within the housing main body 24 prior to use near the proximal end 28 and is visible in part from the exterior through the housing 23 below label 34. Prior to device 20 being used for an injection, and as shown in FIGS. 1 and 2, the syringe 50 is positioned such that the tip 57 of its needle 56 is recessed within the housing 23. During an injection as shown in FIG. 3, the proximal tip 57 is shifted proximally of the housing proximal end 28 for penetrating the user.

Device 20 may use a conventional mechanical drive mechanism to move the syringe 50 from the retracted position shown in FIGS. 1 and 2 to the injecting position shown in FIG. 3, and then to advance the sealing plunger 58 proximally within barrel 52 to force the medication through the outlet tip 57 of needle 56. The particulars of the drive mechanism described below are not material to the present invention, as the injecting progress indicators can be adapted for use with different such mechanisms.

The drive mechanism of device 20 is abstractly shown in FIG. 2 at 60 as including an axially extending plunger element 62, a driver 65, and a trigger assembly 70 that includes button 40. Plunger element 62 has an upper or distal end diagrammatically shown at 75 in FIGS. 2 and 3 that is cooperatively designed with the trigger assembly to be axially retained by the trigger assembly 70 until release by the depressing of button 40. When the plunger element 62 is so released the driver 65, which may be a compression spring already under load, forces the plunger element 62 proximally. When element 62 is so moved, the rod-shaped drive portion 76 of plunger element 62 which fits within the container barrel 52 moves to have its proximal end 77 first close the shown gap 79, and then abut the sealing element 58. Then, the continued driving of plunger element 62 proximally by driver 65 advances the sealing element 58 proximally relative to the housing 23 an identical amount. The movement of the plunger element 62 and sealing plunger 58 first shifts the entire syringe 50 to a needle inserted position shown in FIG. 3 at which further proximal movement of the syringe 50 is prevented. Further movement of plunger element 62 then advances the sealing plunger 58 proximally within the barrel 52 to force medicine from the syringe through needle 56.

Other types of drive mechanisms, such as electromechanical or chemical reaction powered drive mechanisms that work when triggered to shift the plunger element 62 may be employed with the progress indicators of the invention.

The injecting progress indicators 25 include both a flag element and a series of reference features that cooperate with the flag element to provide readily observable information to a user. In the embodiment of FIG. 1, the reference features are provided by four distinct, rounded rectangular viewing windows 82, 83, 84 and 85 that are identically shaped and sized. In FIGS. 2 and 3, these windows 82-85 are shown directly formed in the housing for purposes of illustration, but are actually formed in formed in an opaque part that is visible through the transparent housing 24 as described below with reference to FIG. 13. In an alternate embodiment in which the housing is formed of an opaque material, the windows can be formed by openings in the housing.

Windows 82-85 are spaced axially and in axial alignment. Windows 82-85 are separated and partially defined by opaque bands 90, 91 and 92 of identical shape and size. Each of bands 90-92 is approximately half the axial height of each of windows 82-85 to distinctly set the windows apart.

The flag element of indicators 25 which cooperatively functions with the windows 82-85 is provided by a element that moves within device 20 in response to operation of drive mechanism 60. Flag element in FIG. 2 is formed by a surface 100 on the radially outward side of a rectangular bar 102. When passing within windows 82-85 from the perspective of a user, surface 100 is highly visible outside of device 20. For example, the surface 100 may be colored red if the portions of the device otherwise most visible through windows 82-85 prior to an injection are green. Surface 100 passes through each of windows 82-85 during use in the embodiment of FIGS. 2-3 so as to serve as a single or common flag element for each of the reference features.

Bar 102 is integrally formed with the plunger element 62 that moves axially, but not rotationally, within housing 23. Bar 102 is in radially spaced relationship with rod-shaped drive portion 76 to provide a gap 104 in which the distal flanged end of syringe barrel 52 fits when the plunger element 62 completes its injecting stroke.

Viewing windows 82-85 are axially positioned within device 20 in view of the location of flag element surface 100 immediately prior to the forced flow of medication through needle 56 and the length of the travel of flag element 100 as it moves during the process of satisfactorily emptying the syringe 50 to complete a dose injection. As plunger element 62 and therefore flag element 20 do not rotate within the housing during the injection process, the viewing windows 82-85 are in axial alignment such as shown in FIG. 1. Such alignment can be modified if, for example, the travel of a member on which the flag element is provided is not completely axially during an injection. Moreover, if the angular span of the flag element is sufficient, the viewing windows 82-85 could also be other than in a complete axial alignment, or in other words, they could be angularly offset from each other within the angular expanse of the flag element.

In the embodiment of FIGS. 1-3, the viewing windows are four in number, with viewing windows 82 and 83 being axially located entirely above the syringe 50 prior to syringe movement during the needle insertion process. After needle insertion, syringe 50 is entirely proximal of each of windows 82-84. In alternate embodiments, more, or fewer windows could be provided, so long as such are not confusing to the user. Still further, although shown as being separate windows which are spaced by opaque portions of the material which defines the adjacent windows, the windows could instead be replaced with a single window having a series of conspicuous markings along the axial height of the window. Markings could be on a transparency that overlays the single window, or could be adjacent the window, but in either case would be pronounced so as to be easily visible.

In FIGS. 4-9, the manner in which windows 82-85 or injecting progress indicators 25 appear to a user during the injection process is further illustrated. FIG. 4 shows the injecting progress indicators as arranged when device 20 is as shown in FIG. 3. Flag element surface 100 is not visible to a user as it is disposed distally of all of the viewing windows 82-85 so as not to fill any portion thereof. As the injection progresses, the flag element surface 100 moves down or proximally within the housing 23 simultaneously with and in identical amount as the movement of plunger element 62. This movement causes the lower edge 101 of surface 100 to start to become visible within, and to have surface 100 appear to fill from above, upper window 82, all while leaving the bottom three windows 83-85 unfilled by surface 100. The movement of plunger element 62 is continuous and non-indexed such that flag element surface 100 would appear to steadily move down to fill the window 82. When flag element surface 100 has moved down such that its bottom edge 101 reaches band 90, window 82 appears filled and the indicators 25 appear as shown in FIG. 5.

As the plunger element 62 and flag element surface 100 continue to move downward, surface 100 eventually begins filling window 83 from above, and then when window 83 is approximately halfway so filled the upper edge 103 of surface 100 becomes visible within window 82 which results in surface 100 appearing to be leaving or draining from window 82. The movement continues until the indicators 25 appear as shown in FIG. 6.

This filling and unfilling pattern of the windows continues as shown in FIGS. 7 and 8 up until the point the plunger element 62 has reached the end of its stroke to complete the medication delivery. As such point the injecting progress indicators 25 are configured as shown in FIG. 9 in which window 85 is completely filled by surface 100 and windows 82-84 above are empty, or free, of surface 100. Because the flag element 20 so moves to fill the window and thereby cooperatively completes different injecting progress indicators at different times during the injection, the user will be able to recognize the changing status of the injection, and that when window 85 is filled the injection is complete.

It will be appreciated that the shown filling and then unfilling of windows 82-85 in sequence is merely one way the injecting progress indicators of the present invention may appear to a user during use. For example, if the flag element surface is tall enough, the windows could appear to completely fill up with a vibrant color in sequence, with no emptying of that vibrant color from any window occurring. Moreover, in an alternate embodiment the flag element could cooperate with the windows so as to complete a given indicator by the flag element actually being absent from a window. For example, the flag element could initially fill all the windows prior to use and then appear to complete a window by the flag element unfilling such window as it moves axially in a manner conceptually similar to the arrangement shown in FIGS. 4 through 9. In such an embodiment, the windows would appear to have a color found on the surface 100 drain therefrom.

Figure 12:
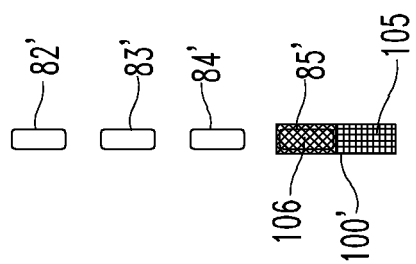
FIG. 12 is a schematic front view similar to the view of FIG. 11 but as configured at a later time at which the complete medication dose has been injected.
Figure 11:
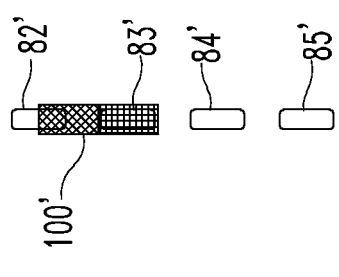
FIG. 11 is a schematic front view similar to the view of FIG. 10 but as configured at a later time during injection than as shown in FIG. 10.
Figure 10:
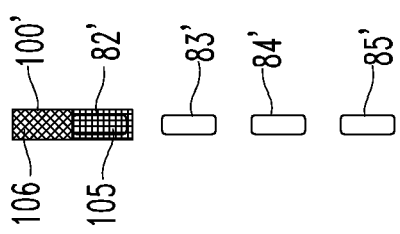
FIG. 10 is a schematic front view of injecting progress indicators of an automatic injection device in another form of the present invention, which indicators are configured at an early stage of an injection.

In still another alternate embodiment shown in FIGS. 10-12 in which related parts to the embodiment of FIGS. 4-9 are denoted with a prime reference, the flag element surface 100' can be provided with first and second colors on different axial portions thereof. A first color 105 and a second color 106, such as green and red, are respectively provided on the proximal and distal halves of the outwardly facing surface 100'. The arrangement of injecting progress indicators shown in FIG. 10 in which first color 105 completely fills window 82' may be prior to device use, or occur shortly after the injection process starts as described with respect to FIGS. 4-9.

As the injection process continues, the flag element 100' fills in succession the windows 82'-85' with first color 105 and then with second color 106 as represented in FIG. 11. When the injection is completed as shown in FIG. 12, the bottom window 85' is completely filled with second color 106, and none of the first color 105 is visible within any window, to show an end of injection having been reached.

Figure 13:
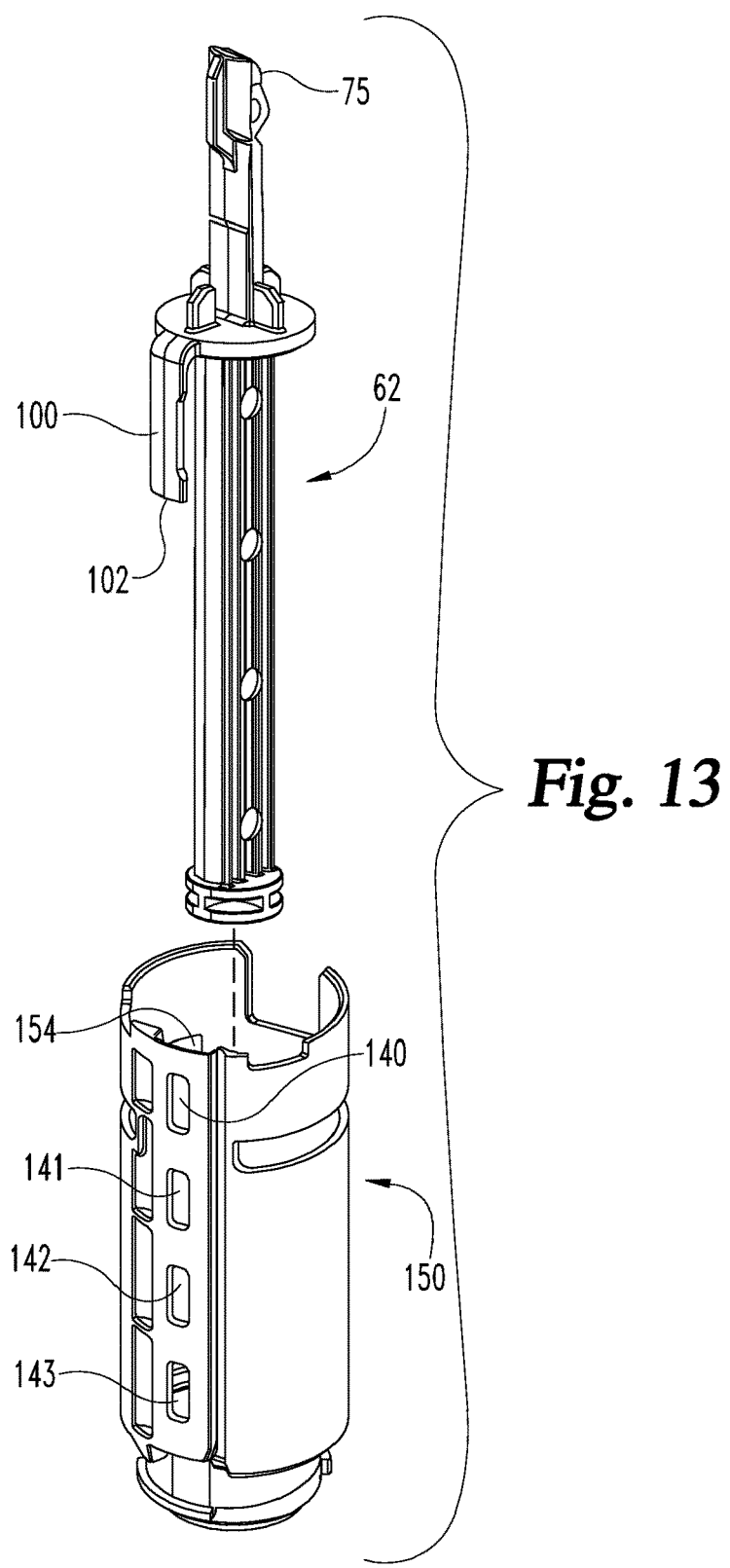
FIG. 13 is an exploded view of select portions of an automatic medication injection which provide injecting progress indicators.

Referring to FIG. 13, there is shown an exploded perspective view of two components of an injection device by which viewing windows 82-85 described with respect to device 20 are readily provided. These device components are related to those disclosed in International Publication No. WO 2014/062488 and are plunger element 62 and a lower shuttle 150. Plunger element 62 is the same as shown in FIGS. 2 and 3 and is therefore referenced the same. Lower shuttle 150 is not shown in FIGS. 2 and 3 and is a part of a delayed syringe retraction feature that may be incorporated in device 20. Lower shuttle 150 is axially stationary within the device housing 23 during an injection, but is moved distally within the device housing after an injection is complete to retract the syringe 50 into the housing.

The windows 82-85 are provided as openings 140, 141, 142 and 143 formed in the opaque lower shuttle 150. The plunger element 62 moves within lower shuttle 150 during injection such that bar 102 slides within a channel 154 radially inward of the openings 140-143. The lower shuttle 150 and its openings 140-142, and that portion of flag element 100 of bar 102 which is is directly radially inward of the openings 140-143, are visible to a user through label opening 38 and the transparent main body 24 of the device housing 23. During an injection, flag member 100 appears to pass through the openings 140-143 to indicate injection progress to a user. When the injection is completed and after the shuttle lower 150 has moved distally within the housing 23, the opening 143 filled by the flag member 100, which serves as the filled window 85, is still visible within the opening 38 provided in the label 34, albeit at a more distal position than prior to the injection.

While this invention has been shown and described as having preferred designs, the present invention may be modified within the spirit and scope of this disclosure. For example, while device 20 provides an automatic needle insertion feature and thus the syringe needle does not project below the proximal end until the device is triggered, the instant injecting progress indicators could be used with an automatic injector in which the needle projects below a housing before use so as to be manually inserted into the user, after which a triggering automatically injects the medicine through the inserted needle. Still further, although the medication injection device 20 is shown as utilizing a container in the form of a syringe having a single outlet needle, the device could utilize different medication containers within the scope of the invention. Moreover, rather than a single needle, different alternative outlets from the container may be utilized within the scope of the invention as its teachings have applicability to other injection devices.

This application is therefore intended to cover any variations, uses or adaptations of the invention using its general principles. Further, this application is intended to cover such departures from the present disclosure as come within known or customary practice in the art to which this invention pertains.

We claim:
1. An automatic medication injection device comprising:
a user grippable housing having a length extending in an axial direction between a proximal end and a distal end;
a container of medication including an outlet that is disposed proximally of said housing proximal end at least during injection, said container including a barrel and a sealing plunger, said sealing plunger in sealing engagement with said barrel;
a drive mechanism within said housing which when triggered is configured to automatically advance said sealing plunger proximally within said container to force medication from the container outlet, said drive mechanism comprising a plunger element being axially movable and non-rotational relative to said housing during injection, said plunger element having a driver portion that extends within said barrel to directly engage said sealing plunger, said plunger element including a proximally extending flag element fixedly coupled thereto, the flag element being in spaced relationship with the plunger element to provide a gap sized to receive a portion of the container; and
a plurality of injecting progress indicators visible along a periphery of the housing, at least one of said plurality of injecting progress indicators located distally of said container during an injection, said injecting progress indicators including the flag element of said plunger element movable as the drive mechanism advances said sealing plunger proximally within said container, said plurality of injecting progress indicators configured to indicate sequentially in an axial direction during a single injection as the flag element moves to cooperatively complete different injecting progress indicators at different times from a start to a finish during the single injection, whereby injecting progress of the single injection may be monitored by a user.

2. The automatic medication injection device of claim 1 wherein said flag element is configured with said drive mechanism to move identically to said sealing plunger when said sealing plunger is advanced within said container, wherein the flag element is configured to move axially, but not rotationally, within said housing during the single injection, wherein said container portion is received by said gap at the finish of the single injection.

3. The automatic medication injection device of claim 2 wherein said flag element is integrally formed with a plunger element of said drive mechanism which directly engages said sealing plunger.

4. The automatic medication injection device of claim 1 wherein said plurality of injecting progress indicators comprises a series of axially spaced windows through which said flag element is visible external to said housing when said flag element moves within said windows.

5. The automatic medication injection device of claim 4 wherein said flag element moves proximally and without rotation within said housing at all times during advancement of said sealing plunger within said container.

6. The automatic medication injection device of claim 4 wherein at different times during the single injection said flag element is visible so as to completely fill only one of said windows.

7. The automatic medication injection device of claim 4 wherein a first region of said flag element is a first color and a second region of said flag element is a second color, said first region being disposed proximally of said second region.

8. The automatic medication injection device of claim 4 wherein said axially spaced windows are visible within an opening defined by a label wrapped on an external periphery of a transparent portion of said housing.

9. The automatic medication injection device of claim 7 wherein at an end of the single injection said second region of said flag element fills a most proximal window of said series of axially spaced windows, and said first region of said flag element is not visible within any window of said series of axially spaced windows.

10. The automatic medication injection device of claim 7 wherein prior to a start of the single injection said first and second regions of said flag element are not visible within any window of said series of axially spaced windows.

11. The automatic medication injection device of claim 4 wherein said series of axially spaced windows are provided in a shuttle member that after injection is movable within said housing in the distal direction.

12. The automatic medication injection device of claim 1 wherein said drive mechanism comprises a plunger element having a driver portion that extends within said container barrel to directly engage said container plunger, said flag element being integrally formed with said plunger element.

13. The automatic medication injection device of claim 12 wherein said flag element is a different color than said driver portion.

14. The automatic medication injection device of claim 12 wherein said flag element does not extend within said container barrel during device use.

* * * * *